US009915587B2

(12) United States Patent
Sugiyama et al.

(10) Patent No.: US 9,915,587 B2
(45) Date of Patent: Mar. 13, 2018

(54) PARTICULATE SENSOR

(71) Applicant: NGK SPARK PLUG CO., LTD., Nagoya-shi, Aichi (JP)

(72) Inventors: Takeshi Sugiyama, Ichinomiya (JP); Masayuki Motomura, Komaki (JP); Keisuke Tashima, Kasugai (JP); Toshiya Matsuoka, Kaizu (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 224 days.

(21) Appl. No.: 14/420,960

(22) PCT Filed: Sep. 10, 2013

(86) PCT No.: PCT/JP2013/074424
§ 371 (c)(1),
(2) Date: Feb. 11, 2015

(87) PCT Pub. No.: WO2014/054390
PCT Pub. Date: Apr. 10, 2014

(65) Prior Publication Data
US 2015/0204759 A1     Jul. 23, 2015

(30) Foreign Application Priority Data
Oct. 4, 2012   (JP) ................. 2012-221931

(51) Int. Cl.
*G01N 15/10*     (2006.01)
*G01M 15/10*     (2006.01)
(Continued)

(52) U.S. Cl.
CPC .......... *G01M 15/102* (2013.01); *G01N 15/06* (2013.01); *G01N 15/0656* (2013.01);
(Continued)

(58) Field of Classification Search
CPC .. G01N 15/102; G01N 15/06; G01N 15/0656; G01N 27/70; G01N 33/0009; G01N 2001/244
See application file for complete search history.

(56) References Cited

U.S. PATENT DOCUMENTS 6,346,179 B1   2/2002   Makino et al.
8,366,813 B2   2/2013   Tokuda et al.
(Continued)

FOREIGN PATENT DOCUMENTS

EP   2228647 A2   9/2010
EP   2500709 A1   9/2012
(Continued)

OTHER PUBLICATIONS

International Search Report of PCT/JP2013/074424 dated Nov. 26, 2013.
(Continued)

*Primary Examiner* — Hezron E Williams
*Assistant Examiner* — David Z Huang
(74) *Attorney, Agent, or Firm* — Sughrue Mion, PLLC

(57) ABSTRACT

A particulate sensor (1) which detects particulates S contained in a gas under measurement (EG) flowing within a gas flow pipe (EP) has a space forming portion (12) and an ion source (15). The space forming portion (12) projects into the gas flow pipe EP and forms an internal space MX. The space forming portion (12) has an introduction port (43I) and a discharge port (48O) for discharging from the internal space MX the gas EGI introduced through the introduction port (43I). The source (15) produces ions CP by gaseous discharge. The space forming portion (12) is configured such that the introduced gas EGI is discharged from the internal space MX through the discharge port (48O), the gas under measurement EG is introduced into the internal space MX (Continued)

through the introduction port (43I), and the introduced gas EGI is mixed with the ions CP produced by the ion source (15).

13 Claims, 9 Drawing Sheets

(51) Int. Cl.
  *G01N 15/06* (2006.01)
  *G01N 27/70* (2006.01)
  *G01N 33/00* (2006.01)
  *G01N 15/00* (2006.01)

(52) U.S. Cl.
  CPC ......... *G01N 27/70* (2013.01); *G01N 33/0009* (2013.01); *G01N 2015/0046* (2013.01)

(56) References Cited

U.S. PATENT DOCUMENTS

| | | |
|---|---|---|
| 8,652,240 B2 | 2/2014 | Sugiyama et al. |
| 2006/0144124 A1 | 7/2006 | Kusaka et al. |
| 2006/0156791 A1 | 7/2006 | Tikkanen et al. |
| 2008/0016946 A1* | 1/2008 | Thanigachalam . G01N 27/4077 73/31.05 |
| 2010/0229724 A1 | 9/2010 | Tokuda et al. |
| 2011/0050243 A1 | 3/2011 | Tikkanen |
| 2012/0234172 A1 | 9/2012 | Sugiyama et al. |
| 2012/0304738 A1* | 12/2012 | Landkammer ..... G01N 15/0656 73/23.33 |

FOREIGN PATENT DOCUMENTS

| | | |
|---|---|---|
| JP | 60-123761 A | 7/1985 |
| JP | 2000-171430 A | 6/2000 |
| JP | 2002-296219 A | 10/2002 |
| JP | 2006-153746 A | 6/2006 |
| JP | 2007-107970 A | 4/2007 |
| JP | 2007-514923 A | 6/2007 |
| JP | 2010-078429 A | 4/2010 |
| JP | 2011-513742 A | 4/2011 |
| JP | 2013-170950 A | 9/2013 |
| WO | 2013/125181 A1 | 8/2013 |

OTHER PUBLICATIONS

Communication dated Jun. 10, 2016, from the European Patent Office in counterpart European Application No. 13843893.2.

* cited by examiner

PARTICULATE SENSOR

CROSS REFERENCE TO RELATED APPLICATIONS

This is a National Stage of International Application No. PCT/JP2013/074424 filed Sep. 10, 2013, claiming priority based on Japanese Patent Application No. 2012-221931 filed Oct. 4, 2012, the contents of all of which are incorporated herein by reference in their entirety.

TECHNICAL FIELD

The present invention relates to a particulate sensor for detecting the amount of particulates contained in a gas under measurement which flows through a gas flow pipe.

BACKGROUND ART

Exhaust gas discharged from an internal combustion engine (for example, a diesel engine or a gasoline engine) may contain particulates such as soot. Exhaust gas containing such particulates is purified by means of collecting the particulates through use of a filter. As the need arises, the filter is heated to a high temperature so as to burn particulates accumulating on the filter to thereby remove them. Therefore, if the filter suffers breakage or a like failure, unpurified exhaust gas is discharged directly to the downstream side of the filter. Therefore, there has been demanded a particulate sensor which can detect particulates contained in exhaust gas in order to directly measure the amount of particulates contained in exhaust gas or to detect a failure of the filter.

For example, Patent Document 1 discloses a particulate measurement method and apparatus. In the method disclosed in Patent Document 1, an ionized gas containing positive ions is mixed with exhaust gas which is introduced from an exhaust pipe into a channel and which contains particulates, so as to electrify the particulates, and the particulates are then released to the exhaust pipe. A current (signal current) which flows in accordance with the amount of the released, charged particulates is detected so as to detect the particulate concentration.

PRIOR ART DOCUMENT

Patent Document

Patent Document 1: Japanese Kohyo (PCT) Patent Publication No. 2011-513742

SUMMARY OF THE INVENTION

Problems to be Solved by the Invention

Incidentally, in such a particulate sensor, introduction and discharge of exhaust gas (gas under measurement), mixing of the exhaust gas with ions, etc. are performed. Therefore, compressed air is needed for operation of its detection section attached to an exhaust pipe. Therefore, a system which uses such a particulate sensor needs a compressed air source, such as a pump, which produces compressed air. However, use of such a compressed air source increases the size of the entire system and increases cost. Also, when a pump or the like is employed as a compressed air source, its service life causes a problem.

The present invention has been accomplished in view of such a problem, and its object is to provide a particulate sensor which performs introduction and discharge of a gas under measurement without using a compressed air source.

Means for Solving the Problems

One mode of the present invention which solves the above-described problems is a particulate sensor having a detection section attached to a gas flow pipe and adapted to detect an amount of particulates contained in a gas under measurement flowing within the gas flow pipe. The detection section includes a space forming portion configured such that, in a state in which the particulate sensor is attached to the gas flow pipe, the space forming portion projects into the gas flow pipe and forms an internal space, the space forming portion having an introduction port for introducing the gas under measurement into the internal space and a discharge port for discharging from the internal space the gas introduced through the introduction port, and an ion source for producing ions by gaseous discharge. The space forming portion is configured such that, through utilization of a negative pressure produced in the discharge port by the gas under measurement flowing within the gas flow pipe, the introduced gas is discharged from the internal space through the discharge port, the gas under measurement is introduced into the internal space through the introduction port, and the introduced gas is mixed with the ions produced by the ion source.

In the present particulate sensor, the space forming portion is configured such that, through utilization of a negative pressure produced in the discharge port by the gas under measurement flowing within the gas flow pipe, the introduced gas is discharged from the internal space through the discharge port, the gas under measurement is introduced into the internal space through the introduction port, and the introduced gas is mixed with the ions produced by the ion source. Accordingly, in this particulate sensor, introduction and discharge of the gas under measurement can be performed without using a compressed air source such as a pump.

Notably, a specific example of the form of the space forming portion is such that the discharge port is provided at a tubular distal end portion which is tapered off. In this case, due to the so-called Venturi effect, the flow velocity of the gas under measurement increases outside the discharge port, whereby a negative pressure is produced in the discharge port.

In the above-describe particulate sensor, preferably, the space forming portion is configured such that the discharge port has an opening at a distal end of the space forming portion and the introduction port has an opening on an outer circumferential surface thereof at a position located on a proximal end side in relation to the discharge port, and, in the state in which the particulate sensor is attached to the gas flow pipe, the axial line of the space forming portion extends within the gas flow pipe in a direction intersecting with a pipe axial line which is the axial line of the gas flow pipe.

In this present sensor, as described above, the space forming portion is formed to extend in a direction intersecting with the pipe axial line, and the discharge port is opened at the distal end thereof. This configuration facilitates the generation of negative pressure in the discharge port. Therefore, introduction and discharge of the gas under measurement can be performed more properly.

Notably, an example of the shape of the space forming portion is a tubular shape.

In the above-described particulate sensor, preferably, the space forming portion has a taper portion which is tapered off, the discharge port is located at a distal end of the taper portion, and, in the state in which the particulate sensor is attached to the gas flow pipe, the facing direction of the opening of the discharge port is orthogonal to the pipe axial line.

In this sensor, the space forming portion has a taper portion which is tapered toward the distal end thereof, and, in a state in which the sensor is attached to the gas flow pipe, the facing direction of the opening formed by the discharge port (the direction in which a surface (imaginary surface) formed by the opening (the discharge port) faces) is orthogonal to the pipe axial line of the gas flow pipe. Through provision of such a taper portion, negative pressure can be produced in the discharge port more efficiently. Therefore, introduction and discharge of the gas under measurement can be performed more properly.

In the above-described particulate sensor, preferably, the space forming portion has the introduction port at each of a plurality of positions dispersed in the circumferential direction of the outer circumferential surface.

In this sensor, the space forming portion has a plurality of introduction ports formed in a proximal end portion of the space forming portion such that they are dispersed in the circumferential direction of the outer circumferential surface thereof. Since a plurality of introduction ports are provided, it is possible to introduce a larger amount of the gas under measurement, to thereby increase the flow rate of the introduced gas flowing from the introduction ports toward the discharge port. Thus, introduction and discharge of the gas under measurement can be performed more properly. Further, in the case where a plurality of introduction ports are provided at equal intervals in the circumferential direction of the outer circumferential surface, the facing directions of the introduction ports in the gas flow pipe cause no problem even when the particulate sensor is fixed to the gas flow pipe through screw engagement.

In any of the above-described particulate sensors, preferably, the ion source is an internal ion source which produces gaseous discharge within the internal space to thereby produce the ions within the internal space.

In this sensor, the ion source produces gaseous discharge within the internal space to thereby produce the ions within the internal space. Therefore, it is possible to mix a large portion of the produced ions with the introduced gas, to thereby cause a larger amount of ions to adhere to the particulates within the introduced gas. Also, since the produced ions are not required to be introduced into the interior space separately, it is unnecessary to provide a compressed air source, an injection hole for injecting ions, etc.

In any of the above-described particulate sensors, preferably, the detection section includes a capturing electrode for capturing floating ions which are a portion of the ions and have not adhered to the particulates through mixing with the introduced gas; and an auxiliary electrode disposed within the internal space and assisting the capturing of the floating ions by the capturing electrode.

When the introduced gas is mixed with the ions generated by the ion source, the ions adhere to particulates contained in the introduced gas, and the particulates with ions adhering thereto (hereinafter referred to as "electrified particulates) are discharged from the discharge port. In the particulate sensor, the amount of particulates contained in the gas under measurement is detected by detecting, in the form of a signal current, the amount of ions adhering to the electrified particulates and discharged from the discharge port. However, if floating ions which is a portion of the ions generated by the ion source and which have not adhered to the particulates are discharged from the discharge port without being caught, a signal current which does not depend on the amount of the particulates increases, and it becomes impossible to properly detect the amount of the particulates. In view of this, a capturing electrode is provided in order to capture the floating ions to thereby prevent the floating ions from being discharged. In addition, the detection section of this sensor has an auxiliary electrode in addition to the capturing electrode. Since this configuration makes it possible to capture the floating ions by the capturing electrode without fail, the amount of the particulates can be detected more properly.

In any of the above-described particulate sensors, preferably, the detection section has a ceramic element which includes an insulating ceramic substrate, and a discharge electrode portion formed unitarily with the ceramic substrate, the discharge electrode portion including a needlelike electrode portion which is exposed from the ceramic substrate and has a needlelike distal end portion, and a lead portion which is located in the ceramic substrate and electrically communicates with the needlelike electrode portion; and the ceramic element is disposed in the space forming portion, produces gaseous discharge by the needlelike electrode portion, and serves as the ion source.

In this sensor, the detection section has a ceramic element in which a discharge electrode portion is formed unitarily with an insulating ceramic substrate and which is disposed in the space forming portion and serves as the ion source. The ceramic element is configured such that a needlelike electrode portion of the discharge electrode portion is exposed from the ceramic substrate. The ceramic element produces gaseous discharge by using the exposed needlelike electrode portion, and serves as the ion source. In this sensor, since the ion source is unitarily formed on the ceramic element in advance, the incorporation of the ion source into the detection section becomes easier, and the particulate sensor can be manufactured at low cost and with high productivity. Notably, examples of the shape of the ceramic substrate which constitutes the ceramic element include a platelike shape, a circular columnar shape, a cylindrical tubular shape, a square columnar shape, and a hexagonal columnar shape. When the ceramic substrate has a platelike shape, the ceramic substrate can be easily formed by stacking and cutting ceramic sheets, whereby the ceramic element can be manufactured at low cost.

In any of the above-described particulate sensors, preferably, the needlelike electrode portion has a plurality of needlelike distal end portions.

In this sensor, the needlelike electrode portion has a plurality of needlelike distal end portions. Since the number of portions used for producing gaseous discharge increases, it becomes possible to more efficiently produce gaseous discharge so as to more efficiently produce ions. Also, since the durability of the needlelike distal end portions against erosion is enhanced, gaseous discharge can be produced stably for a long period of time.

In any of the above-described particulate sensors, preferably, the detection section includes a capturing electrode for capturing floating ions which are a portion of the ions and have not adhered to the particulates through mixing with the introduced gas; and the ceramic element has an auxiliary electrode at a position shifted from the needlelike electrode portion toward the discharge port, the auxiliary electrode assisting the capturing of the floating ions by the capturing electrode.

This sensor has not only a capturing electrode but also an auxiliary electrode at a position shifted from the needlelike electrode portion of the ceramic element toward the discharge port. Therefore, the floating ions can be captured by the capturing electrode without fail.

In the above-described particulate sensor, preferably, the auxiliary electrode is embedded in the ceramic substrate.

In this sensor, the auxiliary electrode is embedded in the ceramic substrate. Therefore, the auxiliary electrode is protected by the ceramic substrate, whereby corrosion or the like of the auxiliary electrode can be prevented.

In any of the above-described particulate sensors, preferably, the ceramic element has a heater for heating the needlelike electrode portion.

In this sensor, the ceramic element has a heater. Therefore, foreign substances, such as water droplets and soot, adhering to the needlelike electrode portion exposed from the ceramic element and a region around the needlelike electrode portion can be removed by heating the foreign substances using the heater, whereby the insulation performance of the ion source having deteriorated can be restored.

In any of the above-described particulate sensors, preferably, the heater is embedded in the ceramic substrate.

In this sensor, the heater is embedded in the ceramic substrate. Therefore, the heater is protected by the ceramic substrate, whereby the heater can maintain its stable characteristic.

In any of the above-described particulate sensors, preferably, the ceramic element is formed by co-firing.

In this sensor, the ceramic element is formed by co-firing. Therefore, the ceramic element in which the discharge electrode portion, etc. are properly united with the ceramic substrate can be readily obtained.

MODE FOR CARRYING OUT THE INVENTION

Figure 1:
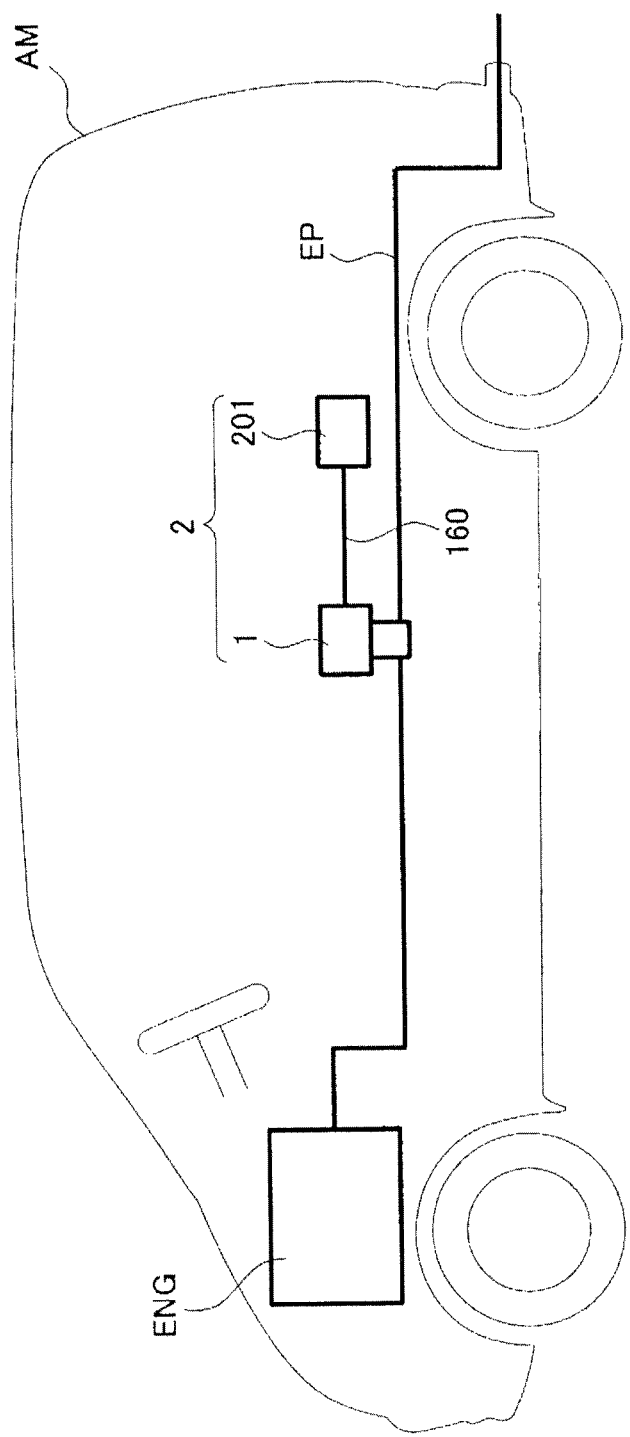
FIG. 1 Explanatory view relating to an embodiment and showing a state in which a particulate detection system including a particulate sensor is applied to an exhaust pipe of an engine mounted on a vehicle.

A particulate detection system 2 including a particulate sensor 1 according to the present embodiment will be described with reference to the drawings. The particulate sensor 1 of the present embodiment is attached to an exhaust pipe EP of an engine ENG (an internal combustion engine) mounted on a vehicle AM, and detects the amount of particulates S (soot, etc.) contained in the exhaust gas EG flowing through the exhaust pipe EP (see FIG. 1). The particulate sensor 1 has a detection section 10 which comes into contact with the exhaust gas EG. In addition to the particulate sensor 1, a cable 160 connected thereto, a circuit section 201, etc. are provided in order to constitute the particulate detection system 2 (see FIG. 2).

The detection section 10 of the particulate sensor 1 is attached to a mount portion EPT of the exhaust pipe EP (a gas flow pipe) where a mount opening EPO is formed. A portion of the detection section 10 (located on the right side (the distal end side) of the mount portion EPT in FIG. 2) extends into the interior of the exhaust pipe EP through the mount opening EPO and is to come into contact with the exhaust gas EG (a gas under measurement).

Outside the exhaust pipe EP, the circuit section 201 is connected to the detection section 10 of the particulate sensor 1 through the cable 160 composed of a plurality of wires. This circuit section 201 includes a circuit which drives the detection section 10 and detects a signal current Is which will be described later.

First, the electrical configuration of the circuit section 201 of the particulate detection system 2 will be described with reference to FIG. 2. The circuit section 201 includes a measurement control circuit 220, an ion source power supply circuit 210, and an auxiliary electrode power supply circuit 240. The ion source power supply circuit 210 has a first output terminal 211 maintained at a first potential PV1 and a second output terminal 212 maintained at a second potential PV2. Specifically, the second potential PV2 is set to a positive high potential in relation to the first potential PV1. More specifically, a pulse voltage (1 to 2 kV0-p) which is positive in relation to the first potential PV1 is output from the second output terminal 212. The pulse voltage is obtained through half-wave rectification of a sinusoidal wave of about 100 kHz. Notably, the ion source power supply circuit 210 constitutes a constant-current power supply whose output current is feedback-controlled such that the output current (rms value) is autonomously maintained at a predetermined current value (for example, 5 μA).

The auxiliary electrode power supply circuit 240 has an auxiliary first output terminal 241 which communicates with the first output terminal 211 and is maintained at the first potential PV1, and an auxiliary second output terminal 242 which is maintained at an auxiliary electrode potential PV3. Specifically, the auxiliary electrode potential PV3 is set to a potential of, for example, DC 100 to 200 V which is a positive high DC potential in relation to the first potential PV1 but is lower than the peak potential (1 to 2 kV) of the second potential PV2.

A signal current detection circuit 230, which partially constitutes the measurement control circuit 220, has a signal input terminal 231 connected to the first output terminal 211 of the ion source power supply circuit 210, and a ground input terminal 232 connected to a ground potential PVE.

This signal current detection circuit 230 is a circuit for detecting the signal current Is flowing between the signal input terminal 231 and the ground input terminal 232.

In the circuit section 201, the ion source power supply circuit 210 and the auxiliary electrode power supply circuit 240 are surrounded by an inner circuit casing 250, which is maintained at the first potential PV1. The first output terminal 211 of the ion source power supply circuit 210, the auxiliary first output terminal 241 of the auxiliary electrode power supply circuit 240, and the signal input terminal 231 of the signal current detection circuit 230 are connected to the inner circuit casing 250. Notably, in the present embodiment, the inner circuit casing 250 accommodates and surrounds the ion source power supply circuit 210, the auxiliary electrode power supply circuit 240, and a secondary-side core 271B of an isolation transformer 270, and electrically communicates with a first potential wiring line 165 of the cable 160.

The isolation transformer 270 has a core 271 which is divided into a primary-side core 271A, around which a primary-side coil 272 is wound, and the above-mentioned secondary-side core 271B, around which a power-supply-circuit-side coil 273 and an auxiliary-electrode-power-supply-side coil 274 are wound. The primary-side core 271A electrically communicates with the ground potential PVE, and the secondary-side core 271B electrically communicates with the first potential PV1 (the first output terminal 211 of the ion source power supply circuit 210).

The ion source power supply circuit 210, the auxiliary electrode power supply circuit 240, the inner circuit casing 250, and the measurement control circuit 220 including the signal current detection circuit 230 are surrounded by an outer circuit casing 260, which electrically communicates with the ground input terminal 232 of the signal current detection circuit 230 and is maintained at the ground potential PVE. The ground input terminal 232 of the signal current detection circuit 230 and the primary-side core 271A of the isolation transformer 270 are connected to the outer circuit casing 260. Notably, in the present embodiment, the outer circuit casing 260 accommodates and surrounds the ion source power supply circuit 210, the auxiliary electrode power supply circuit 240, the inner circuit casing 250, the measurement control circuit 220 including the signal current detection circuit 230, and the primary-side core 271A of the isolation transformer 270. The outer circuit casing 260 electrically communicates with a ground potential wiring line 167 of the cable 160.

The measurement control circuit 220 includes a regulator power supply PS. This regulator power supply PS is driven by an external battery BT through a power supply wiring line BC. The measurement control circuit 220 includes a microprocessor 202, and can communicate, through a communication line CC, with a control unit ECU which controls the internal combustion engine. Thus, the measurement control circuit 220 can transmit to the control unit ECU a signal which represents the result of measurement by the above-mentioned signal current detection circuit 230 (the magnitude of the signal current Is), a value which is converted therefrom and represents the amount of particulates, etc., or the result of determination as to whether or not the amount of particulates exceeds a predetermined amount. This enables the control unit ECU to control the internal combustion engine and perform other operations such as issuance of a warning which reports a failure of a filter (not shown).

A portion of the electric power externally supplied to the measurement control circuit 220 via the regulator power supply PS is distributed to the ion source power supply circuit 210 and the auxiliary electrode power supply circuit 240 via the isolation transformer 270. Notably, in the isolation transformer 270, the primary-side coil 272, which is a portion of the measurement control circuit 220, the power-supply-circuit-side coil 273, which is a portion of the ion source power supply circuit 210, the auxiliary-electrode-power-supply-side coil 274, which is a portion of the auxiliary electrode power supply circuit 240, and the core 271 (the primary-side core 271A and the secondary-side core 271B) are isolated from one another. Therefore, whereas electric power can be distributed from the measurement control circuit 220 to the ion source power supply circuit 210 and the auxiliary electrode power supply circuit 240, the insulation thereamong can be maintained. Notably, in the present embodiment, the isolation transformer 270 also serves as an auxiliary electrode isolation transformer for supplying electric power to the auxiliary electrode power supply circuit 240.

Next, the cable 160 will be described (see FIG. 2). A second potential wiring line 161 and an auxiliary potential wiring line 162, which are formed of copper wire, are disposed at the center of the cable 160. These wiring lines are circumferentially surrounded by the first potential wiring line 165 and the ground potential wiring line 167, each formed of braided thin copper wires, with an unillustrated insulator layer disposed between the wiring lines 161 and 162 and the wiring lines 165 and 167.

Figure 2:
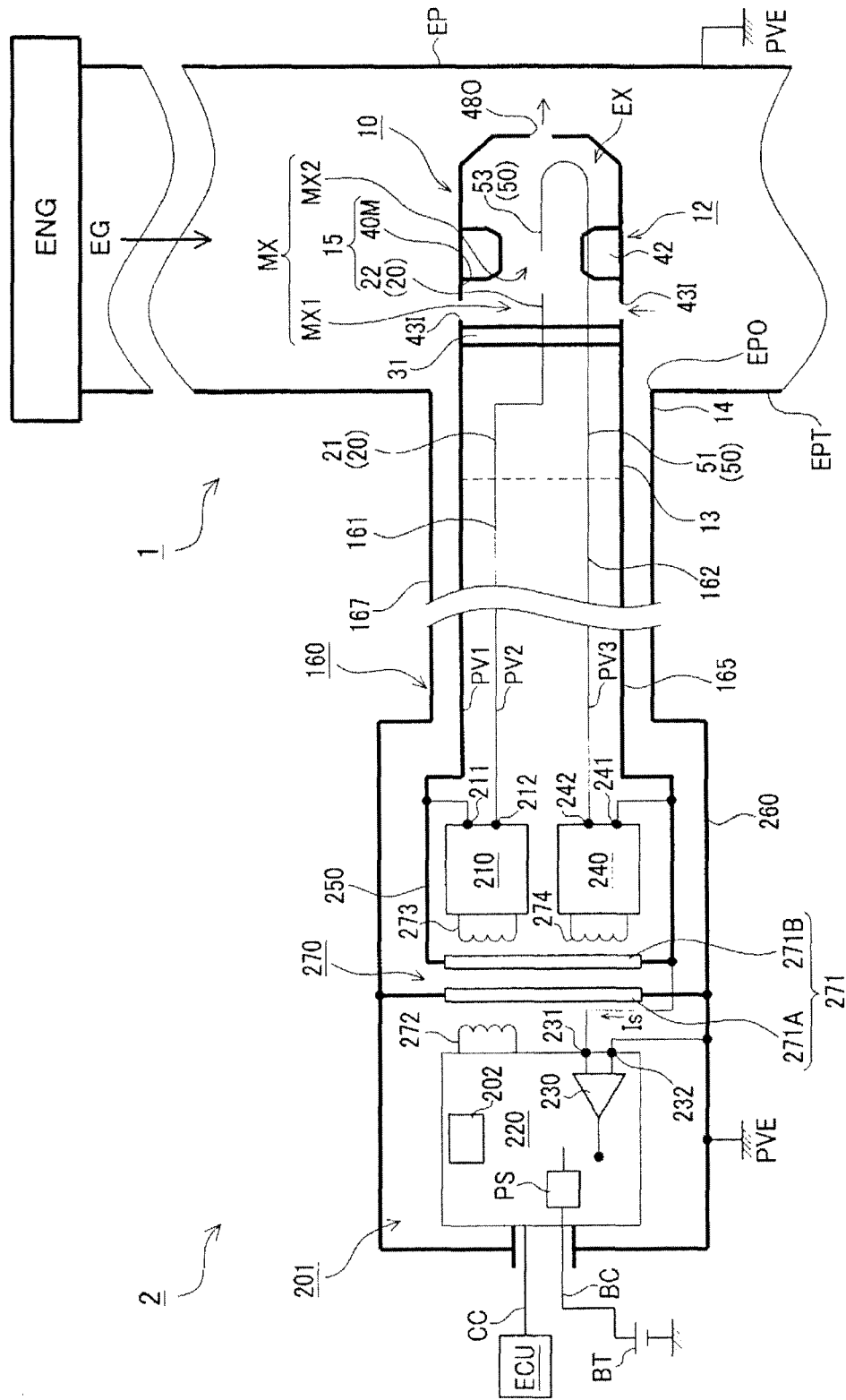
FIG. 2 Explanatory view schematically showing the configuration of the particulate detection system including the particulate sensor according to the embodiment.

As described above, the circuit section 201 is connected to this cable 160 (see FIG. 2). Specifically, the second output terminal 212 of the ion source power supply circuit 210 is maintained at the second potential PV2, and is connected to the second potential wiring line 161 so as to electrically communicate therewith. The auxiliary second output terminal 242 of the auxiliary electrode power supply circuit 240 is maintained at the auxiliary electrode potential PV3, and is connected to the auxiliary potential wiring line 162 so as to electrically communicate therewith. The first output terminal 211 of the ion source power supply circuit 210 is maintained at the first potential PV1, and is connected, for electrical communication, to the auxiliary first output terminal 241 of the auxiliary electrode power supply circuit 240, the signal input terminal 231 of the signal current detection circuit 230, the inner circuit casing 250, and the first potential wiring line 165. The ground input terminal 232 of the signal current detection circuit 230 is connected, for electrical communication, to the outer circuit casing 260 and the ground potential wiring line 167, whereby the ground input terminal 232 is maintained at the ground potential PVE.

Next, the mechanical structure of the detection section 10 of the particulate sensor 1 will be described with reference to the vertical cross sectional views of FIGS. 3 and 4. Notably, the upper side in FIGS. 3 and 4 will be referred to as the "distal end side," and the lower side in FIGS. 3 and 4 will be referred to as the "proximal end side." The mechanical structure of a portion of the detection section 10 located on the proximal end side (the lower side in the drawings) not illustrated in FIGS. 3 and 4 will not be described herein.

As described above, the detection section 10 of the particulate sensor 1 is attached to the mount portion EPT of the exhaust pipe EP (a gas flow pipe) of the engine ENG (an internal combustion engine), the mount portion EPT having the mount opening EPO, and is to come into contact with the exhaust gas EG (a gas under measurement). From the viewpoint of the electrical functions of the detection section 10, the detection section 10 is mainly composed of an ion source 15, a particulate electrification section 12, a first conduction member 13, a needlelike electrode member 20, and an auxiliary electrode member 50.

Figure 3:
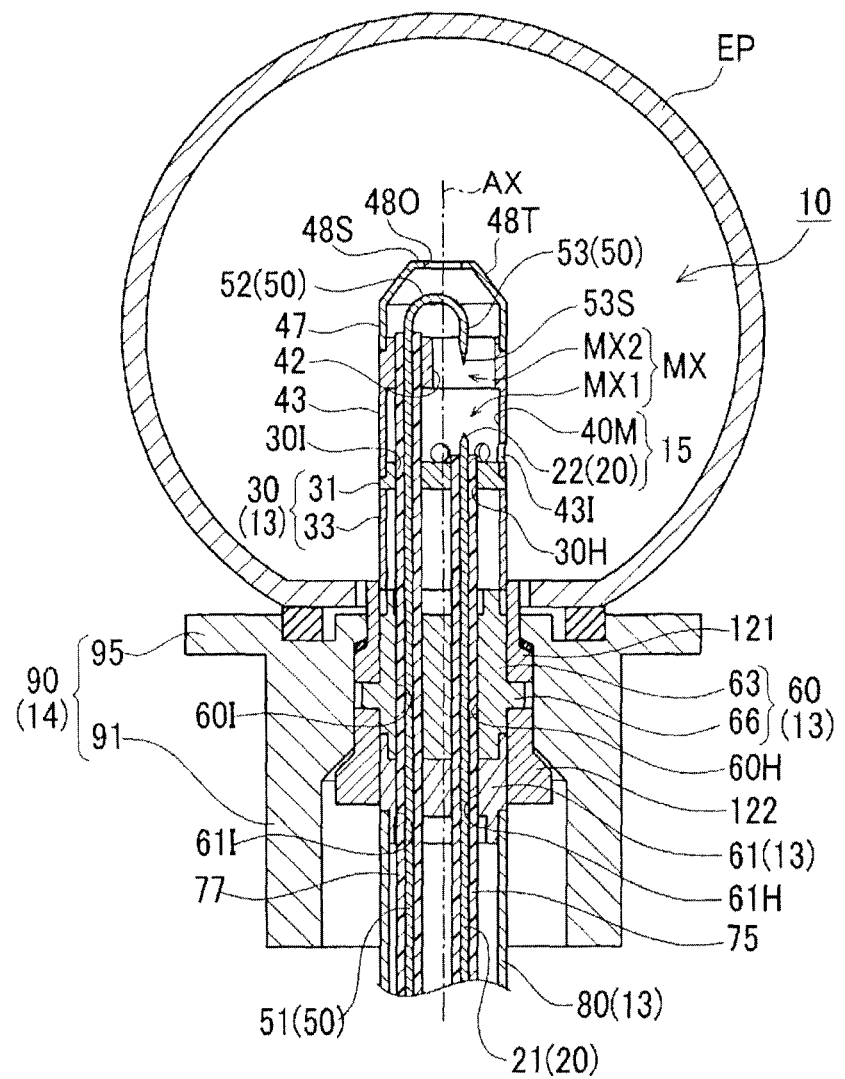
FIG. 3 Vertical sectional view showing the structure of the particulate sensor according to the embodiment.
Figure 4:
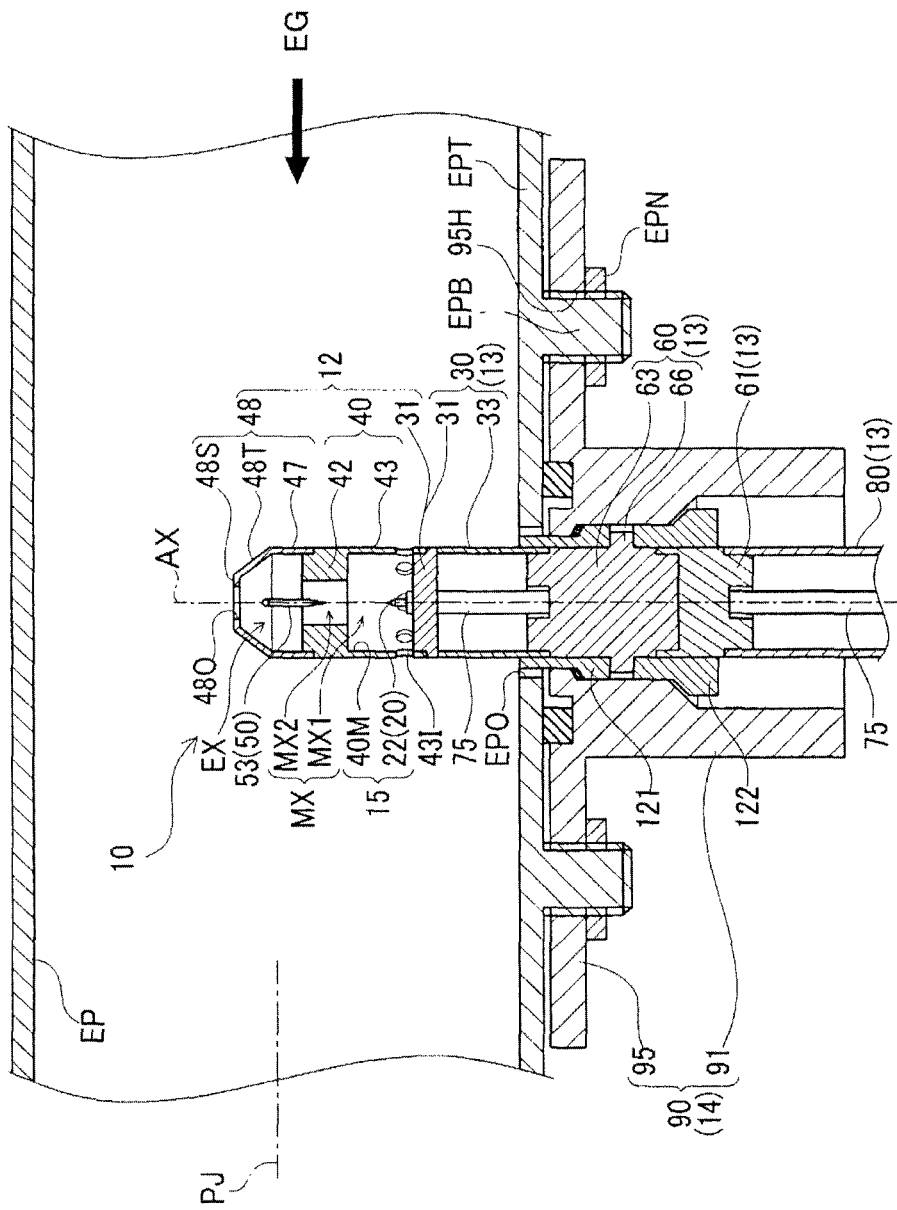
FIG. 4 Vertical cross sectional view at a vertical cross section orthogonal to the cross section of FIG. 3, the vertical cross sectional view showing the structure of the particulate sensor according to the embodiment.

An inner tube 80 which is formed of a metal and has the shape of a hollow cylindrical tube is fitted onto a distal end portion of the cable 160 (not shown in FIGS. 3 and 4). The inner tube 80 is connected to the first potential wiring line 165 of the cable 160 for electrical communication with the first potential wiring line 165, whereby the inner tube 80 is maintained at the first potential PV1. Further, as shown in FIGS. 3 and 4, a second pipe holder 61 formed of a metal (which will be described later) is fitted into a distal end portion of the inner tube 80.

A distal end portion (not shown in FIGS. 3 and 4) of the second potential wiring line 161 of the cable 160 is connected to an extending portion 21 of the needlelike electrode member 20 inside the inner tube 80. This needlelike electrode member 20 is formed of tungsten wire, and has the extending portion 21 and a needlelike distal end portion 22. The extending portion 21 generally has the shape of a straight bar. The needlelike distal end portion 22 is located at the distal end (the upper end in the drawings) of the extending portion 21, and is formed to have a sharp point like a needle. The circumference of the extending portion 21 of the needlelike electrode member 20 is covered by a cylindrical tubular, needlelike electrode insulating pipe 75 formed of an insulating ceramic such as alumina. The extending portion 21 is passed through needlelike electrode insertion holes 60H and 61H formed in a first pile holder 60 formed of a metal and the second pipe holder 61, and is held by the first pile holder 60 and the second pipe holder 61 together with the needlelike electrode insulating pipe 75.

In addition, a distal end portion (not shown in FIGS. 3 and 4) of the auxiliary potential wiring line 162 of the cable 160 is connected to an extending portion 51 of the auxiliary electrode member 50 inside the inner tube 80. The auxiliary electrode member 50 is formed of stainless steel wire, and has the extending portion 51 generally having the shape of a straight bar, a bent portion 52 provided at the distal end of the extending portion 51 and bent back to have a U-like shape, and an auxiliary electrode portion 53 (an auxiliary electrode). Notably, a distal end portion of the auxiliary electrode portion 53 is also formed to have a sharp point like a needle. This distal end portion will be referred to as a needlelike distal end portion 53S. The circumference of the extending portion 51 of the auxiliary electrode member 50 is covered by a cylindrical auxiliary electrode insulating pipe 77 which is formed of an insulating ceramic such as alumina. The extending portion 51 is passed through auxiliary electrode insertion holes 60I and 61I formed in the first pile holder 60 and the second pipe holder 61, and is held by the first pile holder 60 and the second pipe holder 61 together with the auxiliary electrode insulating pipe 77.

The first and second pipe holders 60 and 61 shown in FIGS. 3 and 4 are formed of stainless steel. The first pipe holder 60 has a main body portion 63 generally having the shape of a circular column, and an annular holder flange portion 66 extending radially outward from the main body portion 63 at a position offset toward the proximal end thereof. The second pipe holder 61 generally having the shape of a circular column is fitted onto a proximal end portion of the first pipe holder 60, and is united therewith. The first and second pipe holders 60 and 61 have the needlelike electrode insertion holes 60H and 61H and the auxiliary electrode insertion holes 60I and 61I, which extend in the vertical direction in the drawings. As described above, the extending portion 21 of the needlelike electrode member 20 is inserted into and is held in the needlelike electrode insertion holes 60H and 61H, and the extending portion 51 of the auxiliary electrode member 50 is inserted into and is held in the auxiliary electrode insertion holes 60I and 61I. The first pipe holder 60 is fitted into the second pipe holder 61 so that the first pipe holder 60 is fixed to the second pipe holder 61 and electrically communicates therewith. The second pipe holder 61 is fitted into the inner tube 80 so that the second pipe holder 61 is fixed to the inner tube 80 and electrically communicates therewith.

An intermediate tubular member 30 is fitted onto a distal end portion (located on the upper side in the drawings) of the first pipe holder 60. The intermediate tubular member 30 has the form of a cylindrical tube having a bottom on the distal end side thereof. The intermediate tubular member 30 is also formed of stainless steel, and is composed of a bottom portion 31 located on the distal end side, and a cylindrical tubular wall portion 33 extending from the peripheral edge of the bottom portion 31 toward the proximal end side. The bottom portion 31 has a needlelike electrode insertion hole 30H and an auxiliary electrode insertion hole 30I. The extending portion 21 of the needlelike electrode member 20 and the extending portion 51 of the auxiliary electrode member 50, which project from the first pipe holder 60 toward the distal end side, are inserted into and are held in these holes 30H and 30I, respectively. The intermediate tubular member 30 is fitted onto the first pipe holder 60 so that the intermediate tubular member 30 is fixed to the first pipe holder 60 and electrically communicates therewith. The intermediate tubular member 30, the first pipe holder 60, the second pipe holder 61, and the inner tube 80 form a first conduction member 13 which surrounds the extending portion 21 of the needlelike electrode member 20 and the extending portion 51 of the auxiliary electrode member 50, and are maintained at the first potential PV1.

An introducing/mixing member 40 is fitted onto the distal-end-side bottom portion 31 of the intermediate tubular member 30. This introducing/mixing member 40 is also formed of stainless steel, and is composed of a cylindrical tubular wall portion 43 which forms the outer circumferential surface of the introducing/mixing member 40, and a capturing electrode 42 which bulges inward from a distal end portion (located on the upper side in FIG. 4) of the wall portion 43 and which has an increased thickness. The wall portion 43 has a plurality of (8 in the present embodiment) introduction ports 43I (see FIG. 4) formed in a distal end portion of the wall portion 43 such that the introduction ports 43I are dispersed in the circumferential direction thereof. As will be described later, the introduction ports 43I are openings for introducing the exhaust gas EG into a mixing region MX (which will be described later) defined by the bottom portion 31 of the intermediate tubular member 30 and the introducing/mixing member 40.

A cap member 48 is fitted onto a distal end portion of the introducing/mixing member 40. The cap member 48 is composed of a tubular side wall portion 47 connected to the wall portion 43 of the introducing/mixing member 40, a distal end surface 48S located on the distal end side, and a taper portion 48T whose diameter decreases from the side wall portion 47 toward the distal end surface 48S. A discharge port 48O is formed at the center of the distal end surface 48S such that the discharge port 48O is located on the axial line AX of the introducing/mixing member 40. The cap member 48 and the introducing/mixing member 40 are fitted onto the intermediate tubular member 30 so that they are fixed to the intermediate tubular member 30 and electrically communicates therewith. Thus, the cap member 48 and the introducing/mixing member 40 are maintained at the first potential PV1.

A distal end portion of the introducing/mixing member 40 is formed such that the space inside the distal end portion is narrowed by the capturing electrode 42 which bulges inward. Meanwhile, a circular columnar space is formed inside the wall portion 43 on the proximal end side. Thus, an approximately circular columnar space is formed by the bottom portion 31 of the intermediate tubular member 30, the wall portion 43 of the introducing/mixing member 40, and the capturing electrode 42. This space forms a first mixing region MX1 which is a part of the mixing region MX to be described later. Meanwhile, the narrow space defined by the capturing electrode 42 of the introducing/mixing member 40 forms a second mixing region MX2. The space within the cap member 48 located on the distal end side (the upper side in the drawing) of the capturing electrode 42 forms a discharge passage EX which communicates with the discharge port 48O.

The needlelike distal end portion 22 of the needlelike electrode member 20 inserted into the needlelike electrode insertion hole 30H formed in the bottom portion 31 of the intermediate tubular member 30 projects from the needlelike electrode insulating pipe 75 within the first mixing region MX1 of the mixing region MX. When a high voltage is applied between the needlelike distal end portion 22 and the inner circumferential surface 40M of the introducing/mixing member 40 which defines the mixing region MX, gaseous discharge occurs within the mixing region MX, where by $N_2$, $O_2$, etc. in the atmosphere are ionized, whereby positive ions (e.g., $N^{3+}$, $O^{2+}$; hereinafter also referred to as "ions CP") are produced.

Incidentally, as shown in FIG. 4, the introducing/mixing member 40 has a cylindrical tubular shape, and, in a state in which the particulate sensor 1 is attached to the exhaust pipe EP, the axial line AX of the introducing/mixing member 40 extends within the exhaust pipe EP in a direction orthogonal to a pipe axial line PJ, which is the axial line of the exhaust pipe EP. The discharge port 48O is located at the distal end surface 48S of the cap member 48 on the distal end side of the introducing/mixing member 40, and the facing direction of the opening formed by the discharge port 48O (the direction in which a surface (imaginary surface) formed by the opening (the discharge port 48O) faces) is also orthogonal to the pipe axial line PJ. In addition, the cap member 48 has the taper portion 48T which is provided around the discharge port 48O and whose diameter decreases toward the distal end thereof. The exhaust gas EG flows along the pipe axial line PJ within the exhaust pipe EP from the right side toward the left side in FIG. 4. When the exhaust gas EG flowing within the exhaust pipe EP passes through a region around the cap member 48 and the introducing/mixing member 40, its flow velocity increases on the outside of the discharge port 48O, and the so-called Venturi effect produces a negative pressure in the discharge port 48O. Due to this negative pressure, the introduced exhaust gas EGI (exhaust gas introduced into the mixing region MX) is discharged from the discharge port 48O through the discharge passage EX. At the same time, the exhaust gas EG around the introduction ports 43I is taken into the mixing region MX through the introduction ports 43I.

Meanwhile, ions CP are produced as a result of the gaseous discharge within the first mixing region MX1. Therefore, the introduced exhaust gas EGI is mixed with the ions CP in the mixing region MX, and is discharged from the exhaust port 48O through the discharge passage EX.

The extending portion 51 of the auxiliary electrode member 50 and the auxiliary electrode insulating pipe 77 surrounding it extend within the introducing/mixing member 40 to a position located on the distal end side (the upper side in the drawings) of the capturing electrode 42, and the bent portion 52 which is continuous with the extending portion 51 is located within the cap member 48 (the discharge passage EX). The auxiliary electrode portion 53 (the auxiliary electrode) extending toward the proximal end side (the lower side in the drawings) is located in the second mixing region MX2 defined by the capturing electrode 42 of the introducing/mixing member 40.

As shown in FIG. 3, a first insulating spacer 121 which is formed of an insulating ceramic such as alumina and which has an approximately cylindrical tubular shape is disposed on the distal end side (the upper side in the drawings) of the holder flange portion 66 of the first pipe holder 60. The first insulating spacer 121 surrounds the main body portion 63 of the first pipe holder 60 and a connection between the first pipe holder 60 and the intermediate tubular member 30. Also, a second insulating spacer 122 which is formed of an insulating ceramic such as alumina and which has an approximately cylindrical tubular shape is disposed on the proximal end side (the lower side in the drawings) of the holder flange portion 66. The second insulating spacer 122 surrounds a proximal end portion of the first pipe holder 60 and the second pipe holder 61. A metallic shell 90 formed of stainless steel is disposed around these spacers to be located outward of these spacers in the radial direction (in the left-right direction in the drawings).

The metallic shell 90 has a tubular portion 91 and a flange portion 95. The approximately cylindrical tubular portion 91 has a holding hole 91H for holding the first pipe holder 60, the second pipe holder 61, the first insulating spacer 121, and the second insulating spacer 122 therein. Meanwhile, the flange portion 95 is a plate-shaped portion which extends radially outward from a distal end portion of the tubular portion 91 and which has an approximately elliptical outer shape. The flange portion 95 has bolt through holes 95H which penetrate the flange portion 95 in the thickness direction thereof (at two locations in the present embodiment).

When the detection section 10 is mounted, as shown in FIG. 4, the intermediate tubular member 30, the introducing/mixing member 40, etc. are inserted into the exhaust pipe EP through the mounting opening EPO of the mounting portion EPT of the exhaust pipe EP, stud bolts EPB provided adjacent to the mounting opening EPO are passed through the bolt through holes 95H of the flange portion 95, and nuts EPN are attached to the stud bolts EPB for fastening. As a result, the detection section 10, including the metallic shell 90, is fixed to the mounting portion EPT of the exhaust pipe EP. Notably, the metallic shell 90 forms a housing member 14 of the particulate sensor 1 in cooperation with a plurality of members not shown in FIGS. 3 and 4, and electrically communicates with the ground potential wiring line 167 of the cable 160. Accordingly, together with the exhaust pipe EP, the housing member 14 is maintained at the ground potential PVE through the ground potential wiring line 167 of the cable 160 and the outer circuit casing 260.

Figure 5:
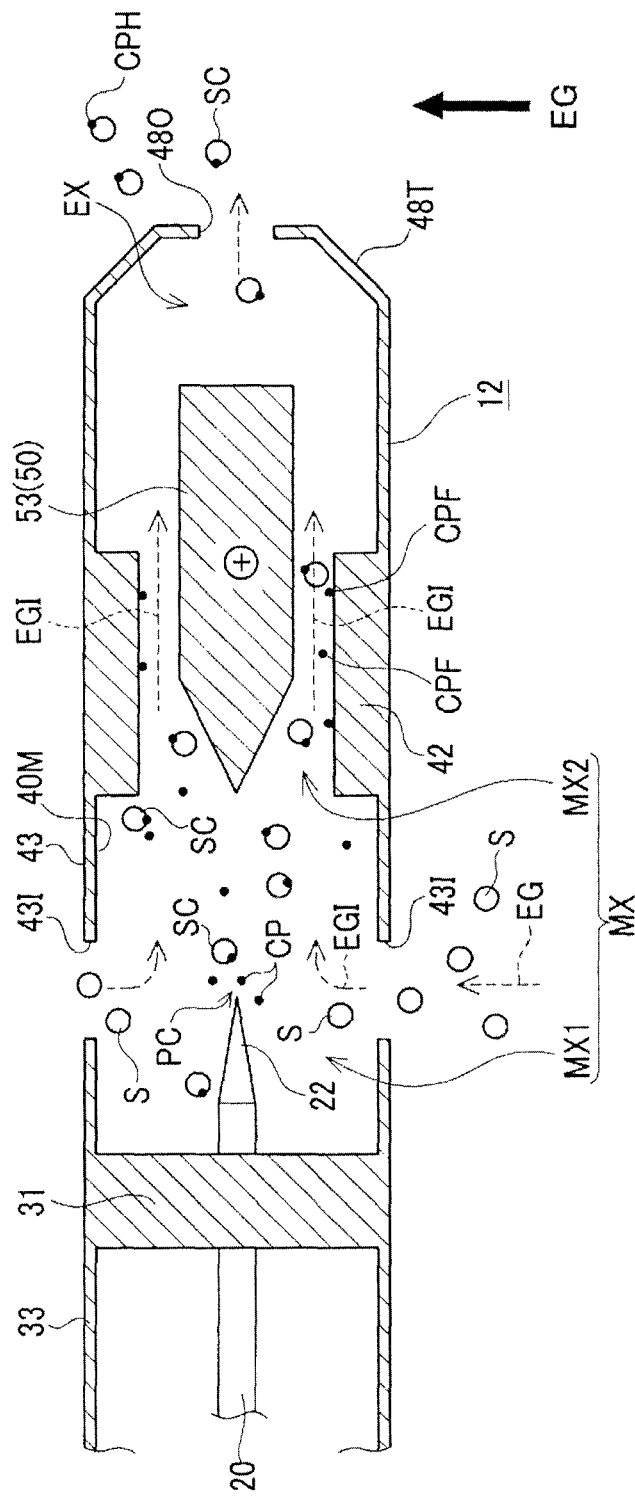
FIG. 5 Explanatory view schematically showing introduction of particulates into a particulate electrification section of the particulate sensor according to the embodiment, electrification of the particulates, and discharge of the electrified particulates from the particulate electrification section.

Next, the electrical functions and operations of various sections of the particulate sensor 1 of the present embodiment will be described with reference to FIG. 5 in addition to FIGS. 2 through 4. FIG. 5 schematically shows the detection section 10 of the present particulate sensor 1 in order to facilitate the understanding of the electrical function and operation thereof.

The needlelike electrode member 20 is connected, for electrical conduction, with the second output terminal 212 of the ion source power supply circuit 210 via the second potential wiring line 161 of the cable 160. Accordingly, as described above, the needlelike electrode member 20 is maintained at the second potential PV2, which is a positive pulse voltage (1 to 2 kV0-p), which is obtained through half-wave rectification of a sinusoidal wave of 100 kHz, in relation to the first potential PV1. Also, the auxiliary electrode member 50 is connected, for electrical conduction, with the auxiliary second output terminal 242 of the auxiliary electrode power supply circuit 240 via the auxiliary potential wiring line 162 of the cable 160. Accordingly, as described above, the auxiliary electrode member 50 is maintained at the auxiliary electrode potential PV3, which is a positive DC potential of 100 to 200 V in relation to the first potential PV1.

Further, the introducing/mixing member 40; the cap member 48; and the inner tube 80, the first pipe holder 60, the second pipe holder 61, and the intermediate tubular member 30, which form the first conduction member 13, are connected, for electrical conduction, with the first output terminal 211 of the ion source power supply circuit 210, the auxiliary first output terminal 241 of the auxiliary electrode power supply circuit 240, the inner circuit casing 250 surrounding these circuits, and the signal input terminal 231 of the signal current detection circuit 230 via the first potential wiring line 165 of the cable 160. These are maintained at the first potential PV1. In addition, the housing member 14 including the metallic shell 90 is connected, for electrical conduction, with the ground input terminal 232 of the signal current detection circuit 230 and the outer circuit casing 260 surrounding the measurement control circuit 220 including the signal current detection circuit 230 via the ground potential wiring line 167 of the cable 160. Thus, the housing member 14 is maintained at the ground potential PVE together with the exhaust pipe EP.

Accordingly, as described above, gaseous discharge (specifically, corona discharge) occurs within the mixing region MX between the inner circumferential surface 40M of the introducing/mixing member 40 maintained at the first potential PV1 and the needlelike distal end portion 22 maintained at the second potential PV2, which is a positive high potential in relation to the first potential PV1. More specifically, positive needle corona PC is produced; i.e., corona is generated around the needlelike distal end portion 22, which serves as a positive electrode. As a result, $N_2$, $O_2$, etc. in the atmospheric air (air) therearound are ionized, whereby positive ions CP are produced. In the present embodiment, the needlelike distal end portion 22 (a distal end portion) of the needlelike electrode member 20 (the needlelike electrode) and the inner circumferential surface 40M of the introducing/mixing member 40 correspond to the ion source 15.

As described above, the cap member 48 and the introducing/mixing member 40 increases the flow velocity of the exhaust gas EG flowing within the exhaust pipe EP, outside the discharge port 48O, to thereby produce negative pressure in the discharge port 48O. Accordingly, due to the negative pressure produced in the discharge port 48O by the exhaust gas EG flowing within the exhaust pipe EP, the introduced exhaust gas EGI within the mixing region MX (the first mixing region MX1, the second mixing region MX2) is discharged from the discharge port 48O through the discharge passage EX. Simultaneously, the exhaust gas EG around the intake ports 43I is taken into the mixing region MX.

At that time, if particulates S such as soot are contained in the exhaust gas EG, as shown in FIG. 5, the particulates S are also introduced into the mixing region MX. Since the generated ions CP are mixed with the introduced exhaust gas EGI within the mixing region MX, the ions CP adhere to the introduced particulates S such as soot, and the particulates S become positively electrified particulates SC. The positively electrified particulates SC flow from the mixing region MX to the discharge port 48O through the discharge passage EX, and are discharged from the discharge port 48O together with the introduced exhaust gas EGI. Meanwhile, of the ions CP produced within the mixing region MX, floating ions CPF not having adhered to the particulates S receive a repulsive force from the auxiliary electrode portion 53 (the auxiliary electrode) of the auxiliary electrode member 50, and adhere to various portions of the introducing/mixing member 40, which is maintained at the first potential PV1 and which forms the capturing electrode 42. As a result, the floating ions CPF are not discharged (are captured).

Accordingly, the amount of the particulates S contained in the exhaust gas EG can be detected by detecting, by the signal current detection circuit 230, the signal current Is which corresponds to the amount of charge of the discharged ions CPH discharged by the electrified particulates SC. In the present embodiment, the particulate electrifying section 12 is formed by the bottom portion 31 of the intermediate tubular member 30, the introducing/mixing member 40, and the cap member 48, which constitute the mixing region MX and the capturing electrode 42. The particulate electrifying section 12 corresponds to the space forming portion. Also, the mixing region MX (the first mixing region MX1, the second mixing region MX2) and the discharge passage EX correspond to the internal space.

As having been described, in the particulate sensor 1 of the present embodiment, the particulate electrification section 12 (the space forming portion) is configured such that, through use of the negative pressure produced in the discharge port 48O by the exhaust gas EG (the gas under measurement) flowing within the exhaust pipe EP, the introduced exhaust gas EGI (the introduced gas) within the mixing region MX (the internal space) is discharged from the discharge port 48O, the exhaust gas EG is introduced into the mixing region MX from the introduction port 33I, and the introduced exhaust gas EGI is mixed with the ions CP produced by the ion source 15. Accordingly, the particulate sensor 1 of the present embodiment can introduce and discharge the exhaust gas EG (the gas under measurement) without use of a compressed air source such as a pump.

In the particulate sensor 1 of the present embodiment, the particulate electrification section 12 has a cylindrical tubular shape, and, in a state in which the sensor 1 is attached to the exhaust pipe EP, the axial line AX of the particulate electrification section 12 extends within the exhaust pipe EP in a direction intersecting with (orthogonal to) the pipe axial line PJ. The discharge port 48O is open at the distal end of the particulate electrification section 12 (the distal end surface 48S of the cap member 48), and the introduction ports 43I are open at the wall portion 43 of the introducing/mixing member 40 which forms the outer circumferential surface of the particulate electrification section 12 located on the proximal end side in relation to the discharge port 48O. Since this configuration facilitates the generation of negative pressure in the discharge port 48O, introduction and discharge of the exhaust gas EG can be performed properly.

In the particulate sensor 1 of the present embodiment, the particulate electrification section 12 has the taper portion 48T which is tapered toward the distal end thereof, and, in a state in which the sensor 1 is attached to the exhaust pipe EP, the facing direction of the opening formed by the discharge port 48O (the direction in which a surface (imaginary surface) formed by the opening (the discharge port 48O) faces) is orthogonal to the pipe axial line PJ of the exhaust pipe EP. Since this configuration enables more efficient generation of negative pressure in the discharge port 48O, introduction and discharge of the exhaust gas EG can be performed more properly.

In the particulate sensor 1 of the present embodiment, the particulate electrification section 12 has a plurality of (8 in the present embodiment) introduction ports 43I formed in the wall portion 43 (which forms the outer circumferential surface of the particulate electrification section 12) such that the introduction ports 43I are dispersed in the circumferential direction of the wall portion 43. Since the plurality of introduction ports 43I are provided, it is possible to introduce a larger amount of the exhaust gas EG (the gas under measurement), to thereby increase the flow rate of the introduced exhaust gas EGI flowing from the introduction ports 43I toward the discharge port 48O. Thus, introduction and discharge of the exhaust gas EG can be performed more properly.

In the particulate sensor 1 of the present embodiment, the ion source 15 produces gaseous discharge within the mixing region MX (the internal space), to thereby produce ions CP within the mixing region MX. As a result, it is possible to mix a large portion of the produced ions CP with the introduced exhaust gas EGI, to thereby cause a larger amount of ions CP to adhere to the particulates S within the introduced exhaust gas EGI. Also, since the produced ions CP are not required to be introduced into the mixing region MX separately, it is unnecessary to provide a compressed air source, an injection hole for injecting the ions CP, etc.

In the particulate sensor 1 of the present embodiment, the detection section 10 includes not only the capturing electrode 42 but also the auxiliary electrode (the auxiliary electrode portion 53 of the auxiliary electrode member 50). Since this configuration enables the capturing electrode 42 to capture floating ions CPF without fail, to thereby allow more proper detection of the amount of the particulates S.

(Modification)

Figure 6:
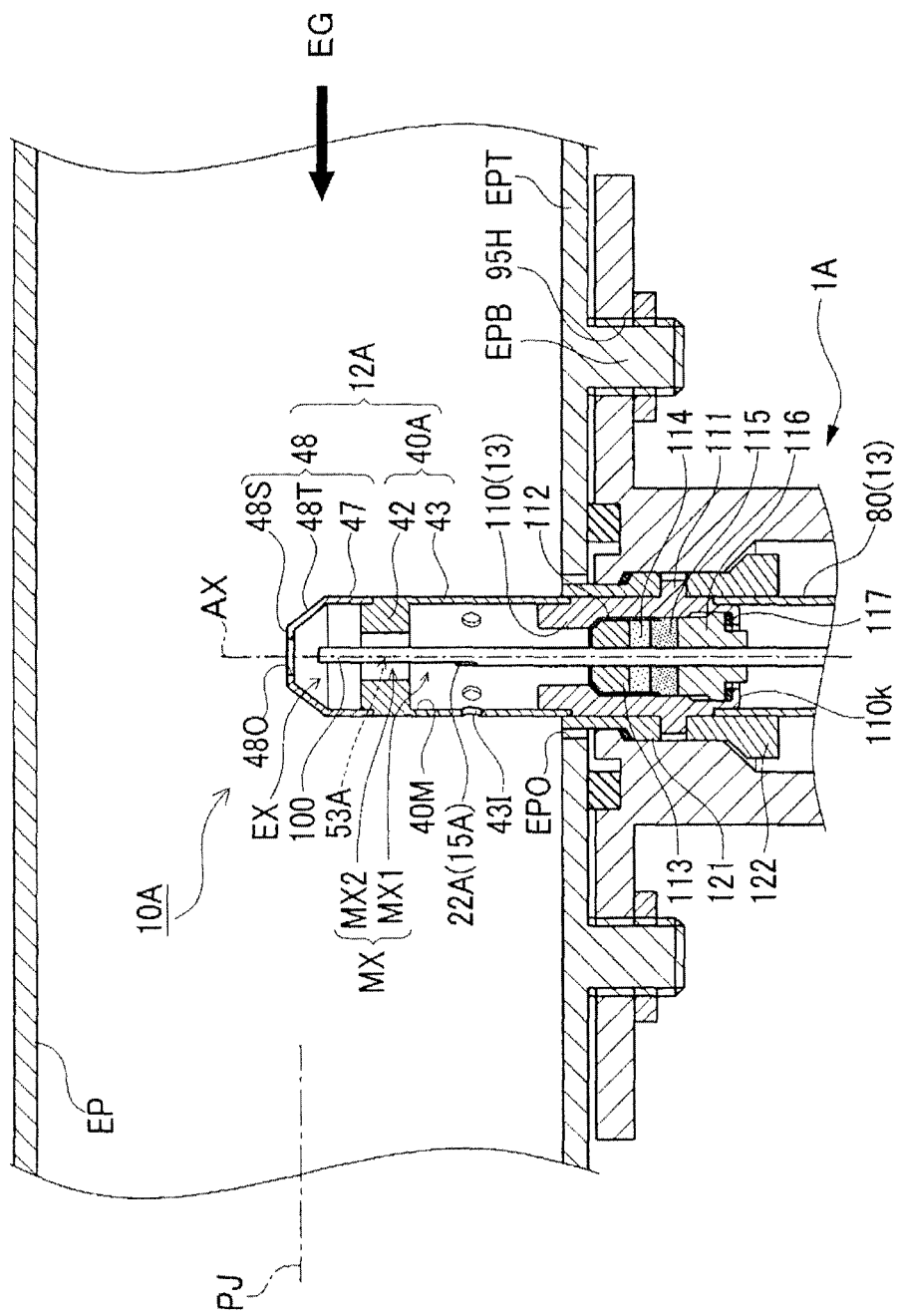
FIG. 6 Vertical sectional view showing the structure of a particulate sensor according to a modification.

Next, a modification of the above-described embodiment will be described with reference to FIGS. 6 through 9. FIG. 6 shows the structure of a particulate sensor 1A according to the present modification. As shown in FIG. 6, a detection section 10A of the particulate sensor 1A according to the present modification does not have a member corresponding to the intermediate tubular member 30 (see FIG. 4) of the embodiment, and has an introducing/mixing member 40A which is slightly longer than the introducing/mixing member 40. Meanwhile, a cap member 48 is the same as the cap member 48 employed in the embodiment, and the introducing/mixing member 40A and the cap member 48 form a particulate electrification section 12A corresponding to the space forming portion. As in the case of the embodiment, a mixing region MX and a capturing electrode 42 are formed in the particulate electrification section 12A. The detection section 10A of the particulate sensor 1A according to the present modification differs from the detection section 10 of the particulate sensor 1 of the embodiment in the point that, instead of the needlelike electrode member 20 and the auxiliary electrode member 50, the detection section 10A includes a rectangular plate-shaped ceramic element 100 in which a discharge electrode portion 20A and an auxiliary electrode portion 50A corresponding to the needlelike electrode member 20 and the auxiliary electrode member 50 are integrally formed and which is disposed in the mixing region MX. Also, the modification differs from the embodiment in the structure which is located outside the exhaust pipe EP and which holds the ceramic element 100.

Figure 7:
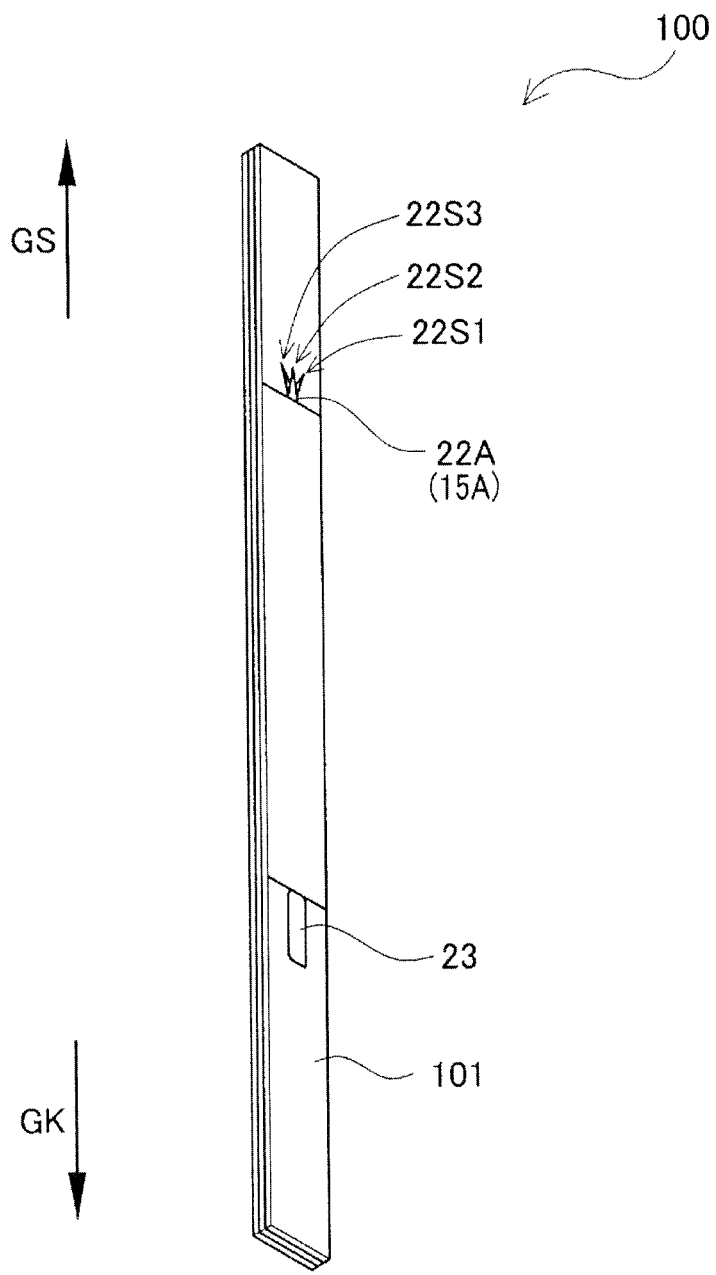
FIG. 7 Perspective view showing the entirety of a ceramic element of the particulate sensor according to the modification.
Figure 8:
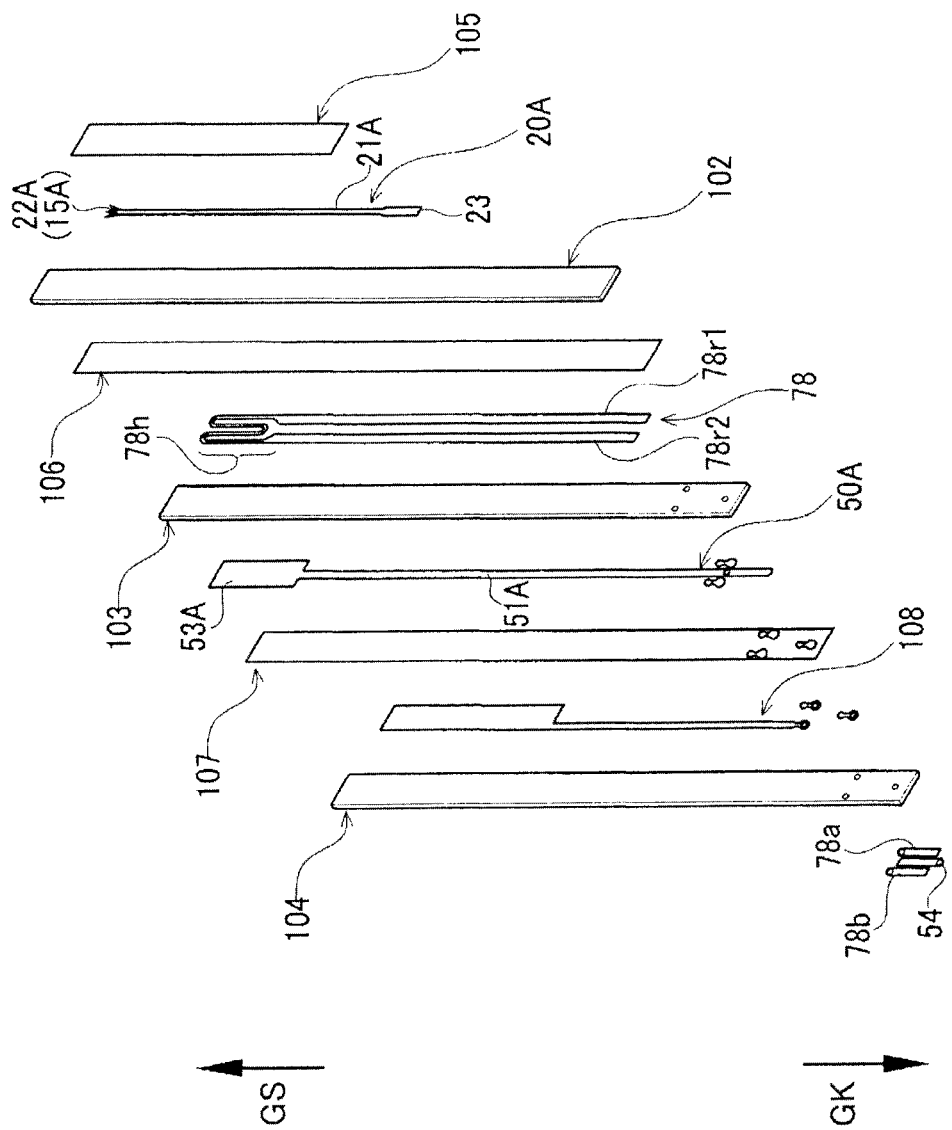
FIG. 8 Exploded perspective view showing the structure of the ceramic element of the particulate sensor according to the modification.

FIG. 7 is an overall view of the ceramic element 100, and FIG. 8 is an exploded perspective view showing the internal structure thereof. The upper side in FIGS. 7 and 8 corresponds to the distal end side GS of the ceramic element 100. The ceramic element 100 is disposed in the mixing region MX such that the distal end side GS is located on the upper side in FIG. 6. First, there will be described the structure of a portion of the detection section 10A of the particulate sensor 1A of the present modification, which portion is located outside the exhaust pipe EP and which holds the ceramic element 100.

As shown in FIG. 6, instead of the first pipe holder 60 and the second pipe holder 61 (see FIG. 4) of the embodiment, a metallic tubular member 110 forming the first conduction member 13 is disposed on the radially inner side of first and second insulating spacers 121 and 122 located outside the exhaust pipe EP. This metallic tubular member 110 has an annular flange portion 111 extending radially outward. This flange portion 111 is fixedly held between the first and second insulating spacers 121 and 122. A proximal end portion (located on the lower side in FIG. 6) of the metallic tubular member 110 is fixedly fitted into an inner tube 80 which forms the first conduction member 13. The introducing/mixing member 40A is fixedly fitted onto a distal end portion (located on the upper side in FIG. 6) of the metallic tubular member 110.

Meanwhile, a metal cup 112 is disposed inside the metallic tubular member 110, and the ceramic element 100 extends through a hole formed in a bottom portion of the metal cup 112. Also, a tubular ceramic holder 113 which is formed of alumina and which holds the ceramic element 100, first and second powder charged layers 114 and 115 each formed by compressing insulating powder, and a tubular ceramic sleeve 116 formed of alumina are disposed around the ceramic element 100 such that these are arranged in this order from the distal end side (the upper side in FIG. 6) toward the proximal end side (the lower side in FIG. 6). Notably, of the members and layers described above, the ceramic holder 113 and the first powder charged layer 114 are located inside the metal cup 112. In the present modification, talc powder is used as the insulating powder used to form the first and second powder charged layers 114 and 115; however, BN (boron nitride) powder, glass powder, vermiculite powder, or the like can be used as the insulating powder.

A crimp ring 117 is disposed between the ceramic sleeve 116 and a proximal end portion 110K of the metallic tubular member 110 located in the inner tube 80. The proximal end portion 110K of the metallic tubular member 110 is bent radially inward for crimping, and presses the ceramic sleeve 116 via the crimp ring 117. As a result, the powder of the second powder charged layer 115 is compressed, whereby the metal cup 112 and the ceramic sleeve 116 are fixed within the metallic tubular member 110, and the ceramic element 100 is supported.

An end portion of the ceramic element 100 located on the proximal end side GK thereof (see FIGS. 7 and 8) is inserted into an unillustrated terminal structure which has lead terminals which are in contact, for electrical communication, with connection terminal portions 23, 54 and heater terminal portions 78a, 78b, which will be described later. As a result, the connection terminal portions 23, 54, etc. of the ceramic element 100 are electrically connected to the ion source power supply circuit 210, etc. through the lead terminals of the terminal structure, the second potential wiring line 161, the auxiliary potential wiring line 162 (see FIG. 2), etc. connected to the lead terminals. In this manner, the ceramic element 100 is attached to the detection section 10A, and is held thereby.

Next, the structure of the ceramic element 100 will be described in detail. As shown in FIGS. 7 and 8, the ceramic element 100 has a plate-shaped insulating ceramic substrate 101 formed of alumina. The discharge electrode portion 20A, the auxiliary electrode portion 50A, and a heater 78 are embedded in the ceramic substrate 101 and are sintered together.

More specifically, the ceramic substrate 101 has three plate-shaped ceramic layers 102, 103, and 104 formed of alumina, and three insulating cover layers 105, 106, and 107 each of which is formed of alumina and is located between adjacent ceramic layers or on the surface of the corresponding ceramic layer. As shown in FIG. 8, the insulating cover layer 105, the ceramic layer 102, the insulating cover layer 106, the ceramic layer 103, the insulating cover layer 107, and the ceramic layer 104 are layered in this order. In FIG. 8, these layers are arranged in this sequence from the upper right to the lower left. The discharge electrode portion 20A is disposed between the insulating cover layer 105 and the ceramic layer 102, the heater 78 is disposed between the insulating cover layer 106 and the ceramic layer 103, and the auxiliary electrode portion 50A is disposed between the ceramic layer 103 and the insulating cover layer 107. Also, a GND layer 108 is formed between the insulating cover layer 107 and the ceramic layer 104 of the ceramic substrate 101. These layers are united together to form the ceramic element 100.

The discharge electrode portion 20A has a needlelike electrode portion 22A for producing gaseous discharge, specifically, corona discharge, a lead portion 21A communicating with the needlelike electrode portion 22A, and a connection terminal portion 23 communicating with the lead portion 21A and used for connection with the second potential wiring line 161 (see FIG. 2) not shown in FIG. 6. The discharge electrode portion 20A is formed on the ceramic layer 102 such that the needlelike electrode portion 22A is located on the distal end side GS of the ceramic element 100 (on the upper side in FIG. 8) and the connection terminal portion 23 is located on the proximal end side GK of the ceramic element 100 (on the lower side in FIG. 8). Notably, the needlelike electrode portion 22A and the connection terminal portion 23 of the discharge electrode portion 20A are exposed on the surface of the ceramic layer 102, and the lead portion 21A of the discharge electrode portion 20A is covered with the insulating cover layer 105.

When a high voltage is applied between the needlelike electrode portion 22A exposed on the ceramic substrate 101 (the ceramic layer 102) and the GND layer 108 within the ceramic substrate 101 through the connection terminal portion 23 and the heater terminal portion 78b which also serves as a GND connection terminal to be described later, corona discharge occurs around the needlelike electrode portion 22A. As a result, the needlelike electrode portion 22A of the ceramic element 100 serves an ion source 15A, whereby ions CP are produced in the mixing region MX as in the case of the embodiment. Notably, the needlelike electrode portion 22A has three needlelike distal end portions 22S1, 22S2, and 22S3. Since the number of portions used for producing corona discharge increases, it is possible to more efficiently produce corona discharge so as to more efficiently produce ions. Also, since the durability of the needlelike distal end portion 22 against erosion is enhanced, corona discharge can be produced stably for a long period of time.

The auxiliary electrode portion 50A has a rectangular auxiliary electrode 53A disposed on the distal end side GS of the ceramic element 100 (on the upper side in FIG. 8), and a lead portion 51A communicating with the auxiliary electrode 53A and extending toward the proximal end side GK of the ceramic element 100 (on the lower side in FIG. 8). A connection terminal portion 54 is provided on the surface of an end portion of the ceramic layer 104 located on the proximal end side GK. The connection terminal portion 54 communicates with the lead portion 51A, and is used for connection with the auxiliary potential wiring line 162 (see FIG. 2) not shown in FIG. 6.

Notably, the auxiliary electrode 53A is disposed in the ceramic element 100 to be located on the distal end side GS in relation to the needlelike electrode portion 22A. Namely, in a state in which the ceramic element 100 is disposed in the detection section 10A (see FIG. 6), the auxiliary electrode 53A is located at a position shifted from the needlelike electrode portion 22A toward the discharge port 48O (the upper side in FIG. 6). As a result, the auxiliary electrode 53A functions in the same manner as the auxiliary electrode of the embodiment. Specifically, when the auxiliary electrode 53A is maintained at a predetermined potential (for example, a positive DC potential of 100 to 200 V in relation to the GND potential of the GND layer 108), the auxiliary electrode 53A applies a repulsive force to the floating ions CPF (ions CP having been produced in the mixing region MX and not having adhered to the particulates S). Thus, the repulsive force forces the floating ions CPF to adhere to various portions of the inner wall of the particulate electrification section 12A which forms the capturing electrode 42, to thereby assist the capturing of the floating ions CPF by the capturing electrode 42. As a result, the floating ions CPF can be captured by the capturing electrode 42 without fail.

The heater 78 has a heat generation portion 78h and two lead portions 78r1 and 78r2. The heat generation portion 78h is disposed on the distal end side GS of the ceramic element 100 such that the heat generation portion 78h surrounds the needlelike electrode portion 22A when the ceramic element 100 is viewed in plan. When electricity is supplied to the heat generation portion 78h, the heat generation portion 78h heats the needlelike electrode portion 22A. The lead portions 78r1 and 78r2 communicate with the heat generation portion 78h, and extend toward the proximal end side GK of the ceramic element 100. Notably, end parts of the heat generation portion 78h which are connected to the lead portions 78r1 and 78r2 extend toward the distal end side GS, and a central part of the heat generation portion 78h is bent back toward the proximal end side GK such that the central portion surrounds the needlelike electrode portion 22A and forms a U-like shape. The heater terminal portions 78a and 78b are formed on the surface of the end portion of the ceramic layer 104 located on the proximal end side GK such that the connection terminal portion 54 of the auxiliary electrode portion 50A is located between the heater terminal portions 78a and 78b. Notably, the heater terminal portion 78b communicates with the GND layer 108 as well, and also serves as the GND connection terminal. When electricity is supplied between the heater terminal portions 78a and 78b of the heater 78, the needlelike electrode portion 22A exposed from the ceramic element 100 is heated. As a result, foreign substances, such as water droplets and soot, adhering to the needlelike electrode portion 22A and a region therearound are removed, whereby the insulation performance of the ion source 15A (the needlelike electrode portion 22A) having deteriorated can be restored.

The ceramic element 100 is formed as follows. First, green sheets which are to become the ceramic layers 102, 103, and 104 are prepared. Next, metal paste is applied, through printing, on one surface of the green sheet which is to become the ceramic layer 102, the surface facing toward the upper rights in FIG. 8, to thereby form the discharge electrode portion 20A. Further, the insulating cover layer 105 is printed on the green sheet which is to become the ceramic layer 102 such that the needlelike electrode portion 22A and the connection terminal portion 23 are exposed, and the lead portion 21A is covered. Also, the heater 78 is printed on one surface of the green sheet which is to become the ceramic layer 103, and the auxiliary electrode portion 50A is printed on the other surface of the green sheet. Further, the insulating cover layer 106 is printed to cover the entirety of the one surface of the green sheet which is to become the ceramic layer 103 and on which the heater 78 has been printed. Also, the GND layer 108 is printed on one surface of the green sheet which is to become the ceramic layer 104, and the connection terminal portion 54 of the auxiliary electrode portion 50A and the heater terminal portions 78a and 78b are printed on the other surface of the green sheet. Further, the insulating cover layer 107 is printed to cover the entirety of the one surface of the green sheet which is to become the ceramic layer 104 and on which the GND layer 108 has been printed.

The green sheets which are to become the ceramic layers 102, 103, and 104 are stacked and are fired together (co-firing), whereby the ceramic element 100 is formed. This co-firing facilitates the obtainment of the ceramic element 100 in which the discharge electrode portion 20A, the auxiliary electrode portion 50A, the heater 78, and the ceramic substrate 101 are properly united.

Figure 9:
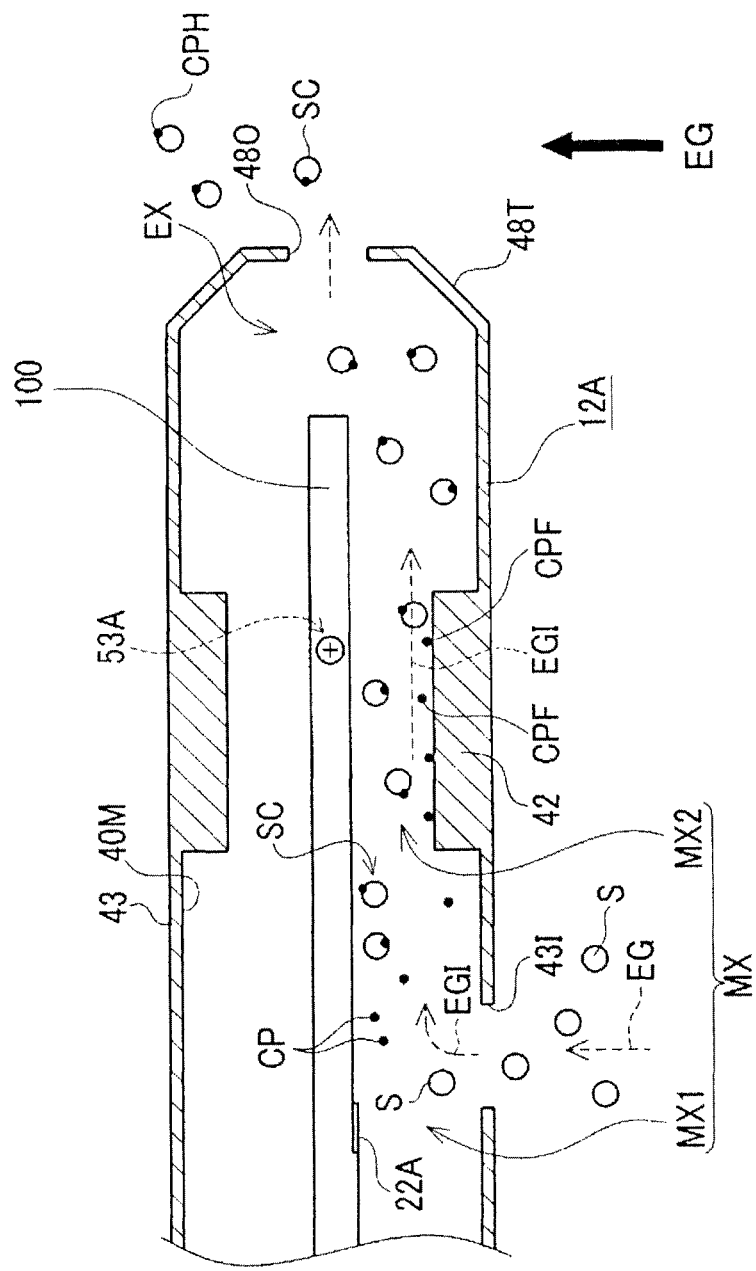
FIG. 9 Explanatory view schematically showing introduction of particulates into a particulate electrification section of the particulate sensor according to the modification, electrification of the particulates, and discharge of the electrified particulates from the particulate electrification section.

Like FIG. 5 for the embodiment, FIG. 9 shows the electrical function and operation of the detection section 10A of the particulate sensor 1A of the present modification. As shown in FIG. 9, when the so-called Venturi effect produces a negative pressure in the discharge port 48O, the exhaust gas EG around the introduction ports 43I is taken into the mixing region MX through the introduction ports 43I. As a result, the ions CP produced by the needlelike electrode portion 22A (the ion source 15A) of the ceramic element 100 adhere to particulates S introduced together with the exhaust gas EG, and become electrified particulates SC. The electrified particulates SC flow from the mixing region MX to the discharge port 48O through the discharge passage EX, and are discharged from the discharge port 48O together with the introduced exhaust gas EGI. Meanwhile, of the ions CP produced within the mixing region MX, floating ions CPF not having adhered to the particulates S receive a repulsive force from the auxiliary electrode portion 53A which is disposed at a position shifted from the needlelike electrode portion 22A of the ceramic element 100 toward the discharge port 48O and which is maintained at a predetermined potential (for example, a positive DC potential of 100 to 200 V). As a result, the floating ions CPF adhere to various portions of the inner wall of the particulate electrification section 12A which constitutes the capturing electrode 42. In this manner, the floating ions CPF are captured by the capturing electrode 42 without being discharged from the discharge port 48O.

As having been described, in the particulate sensor 1A of the present modification, the detection section 10A has the ceramic element 100 in which the discharge electrode portion 20A is formed unitarily with the insulating ceramic substrate 101 and which is disposed in the mixing region MX and serves as the ion source 15A. In this particulate sensor 1A, since the ion source 15A (the needlelike electrode portion 22A) is unitarily formed on the ceramic element 100 in advance, the incorporation of the ion source 15A into the detection section 10A becomes easier, and the particulate sensor 1A can be manufactured at low cost and with high productivity.

Also, in the particulate sensor 1A, the auxiliary electrode 53A and the heater 78 are embedded in the ceramic substrate 101 of the ceramic element 100 and are not exposed to the outside. Since the auxiliary electrode 53A is protected by the ceramic substrate 101, corrosion or the like of the auxiliary electrode 53A can be prevented. Also, since the heater 78 is protected by the ceramic substrate 101, the heater 78 can maintain its stable characteristic.

In the above, the present invention has been described on the basis of the embodiment and modification thereof. However, needless to say, the present invention is not limited to the above-described embodiment, etc., and may be modified freely without departing from the scope of the invention.

For example, in the above-described embodiment, the detection section 10 of the particulate sensor 1 is connected to the circuit section 201 of the particulate detection system 2 through the cable 160. However, the embodiment may be modified freely, for example, such that the detection section 10 and the circuit section 201 are connected directly (united together) without providing the cable 160 therebetween.

DESCRIPTION OF SYMBOLS

EP: exhaust pipe (gas flow pipe)
EPO: mount opening
EG: exhaust gas (gas under measurement)
EGI: introduced exhaust gas (introduced gas)
S: particulate
SC: electrified particulate
CP: ion
CPF: floating ion
CPH: discharged ion
Is: signal current
1, 1A: particulate sensor
2: particulate detection system
10, 10A: detection section
12, 12A: particulate electrification section (space forming portion)
15, 15A: ion source
20: needlelike electrode member
21: extending portion (of the needlelike electrode member)
22: needlelike distal end portion (of the needlelike electrode member) (ion source)
20A: discharge electrode portion
21A: lead portion (of the discharge electrode portion)
22A: needlelike electrode portion (ion source)
22S1, 22S2, 22S3: needlelike distal end portion
30: intermediate tubular member (first conduction member)
31: bottom portion of (the intermediate tubular member) (particulate electrification section)
PV1: first potential
PV2: second potential
PV3: auxiliary electrode potential
PVE: ground potential
40, 40A: introducing/mixing member (particulate electrification section)
40M: inner circumferential surface (of the introducing/mixing member) (ion source)

MX: mixing region (internal space)
MX1: first mixing region (internal space)
MX2: second mixing region (internal space)
EX: discharge passage (internal space)
42: capturing electrode
43: tubular wall portion (of the mixing/discharging member) (outer circumferential surface)
43I: introduction port
48: cap member (particulate electrification section)
48O: discharge port
48T: taper portion
50: auxiliary electrode member
53: auxiliary electrode portion (of the auxiliary electrode member) (auxiliary electrode)
50A: auxiliary electrode portion
53A: auxiliary electrode
60: first pipe holder (first conduction member)
61: second pipe holder (first conduction member)
80: inner sleeve (first conduction member)
90: metallic shell (housing)
201: circuit section
210: ion source power supply circuit
220: measurement control circuit
230: signal current detection circuit
240: auxiliary electrode power supply circuit
100: ceramic element
101: ceramic substrate
78: heater

The invention claimed is:

1. A particulate sensor having a detection section attached to a gas flow pipe and adapted to detect an amount of particulates contained in a gas under measurement flowing within the gas flow pipe, wherein
the detection section includes:
a space forming portion configured such that, in a state in which the particulate sensor is attached to the gas flow pipe, the space forming portion projects into the gas flow pipe and forms an internal space, the space forming portion having an introduction port for introducing the gas under measurement into the internal space and a discharge port for discharging from the internal space the gas introduced through the introduction port, and
an ion source for producing ions by gaseous discharge;
the detection section further includes a capturing electrode for capturing floating ions which are a portion of the ions and have not adhered to the particulates through mixing with the introduced gas,
the space forming portion is configured such that, through utilization of a negative pressure produced in the discharge port by the gas under measurement flowing within the gas flow pipe, the introduced gas is discharged from the internal space through the discharge port, the gas under measurement is introduced into the internal space through the introduction port, and the introduced gas is mixed with the ions produced by the ion source, and
the space forming portion forms the capturing electrode, wherein
the detection section has a ceramic element which includes an insulating ceramic substrate, and a discharge electrode portion formed unitarily with the ceramic substrate, the discharge electrode portion including a needlelike electrode portion which is exposed from the ceramic substrate and has a needlelike distal end portion, and a lead portion which is located within the ceramic substrate and electrically communicates with the needlelike electrode portion; and
the ceramic element is disposed in the space forming portion, produces gaseous discharge by using the needlelike electrode portion, and serves as the ion source.

2. A particulate sensor as claimed in claim 1, wherein the space forming portion is configured such that
the discharge port has an opening at a distal end of the space forming portion and the introduction port has an opening on an outer circumferential surface thereof at a position located on a proximal end side in relation to the discharge port, and
in the state in which the particulate sensor is attached to the gas flow pipe, an axial line of the space forming portion extends within the gas flow pipe in a direction intersecting with a pipe axial line which is an axial line of the gas flow pipe.

3. A particulate sensor as claimed in claim 2, wherein the space forming portion has a taper portion which is tapered off, the discharge port is located at a distal end of the taper portion, and, in the state in which the particulate sensor is attached to the gas flow pipe, a facing direction of the opening of the discharge port is orthogonal to the pipe axial line.

4. A particulate sensor as claimed in claim 2, wherein the space forming portion has the introduction port at each of a plurality of positions dispersed in a circumferential direction of the outer circumferential surface.

5. A particulate sensor as claimed in claim 1, wherein the ion source is an internal ion source which produces gaseous discharge within the internal space to thereby produce the ions within the internal space.

6. A particulate sensor as claimed in claim 1, wherein
the detection section includes: an auxiliary electrode disposed within the internal space and assisting the capturing of the floating ions by the capturing electrode.

7. A particulate sensor as claimed in claim 1, wherein the needlelike electrode portion has a plurality of needlelike distal end portions.

8. A particulate sensor as claimed in claim 1, wherein
the ceramic element has an auxiliary electrode at a position shifted from the needlelike electrode portion toward the discharge port, the auxiliary electrode assisting the capturing of the floating ions by the capturing electrode.

9. A particulate sensor as claimed in claim 8, wherein the auxiliary electrode is embedded in the ceramic substrate.

10. A particulate sensor as claimed in claim 1, wherein the ceramic element has a heater for heating the needlelike electrode portion.

11. A particulate sensor as claimed in claim 10, wherein the heater is embedded in the ceramic substrate.

12. A particulate sensor as claimed in claim 1, wherein the ceramic element is formed by co-firing.

13. A particulate sensor having a detection section attached to a gas flow pipe and adapted to detect an amount of particulates contained in a gas under measurement flowing within the gas flow pipe, wherein
the detection section includes:
a space forming portion configured such that, in a state in which the particulate sensor is attached to the gas flow pipe, the space forming portion projects into the gas flow pipe and forms an internal space, the space forming portion having an introduction port for introducing the gas under measurement into the internal space and a discharge port for discharging from the internal space the gas introduced through the introduction port, and an ion source for producing ions by gaseous discharge of the gas under measurement introduced into the internal space, the ion source being an internal ion source which produces gaseous discharge of the gas under measurement within the internal space to thereby produce ions within the internal space;

the detection section further includes a capturing electrode for capturing floating ions which are a portion of the ions and have not adhered to the particulates through mixing with the introduced gas, the space forming portion is configured such that the gas under measurement is introduced into and discharged from the internal space without the assistance of a compressed air source, the space forming portion is configured such that, through utilization of a negative pressure produced in the discharge port by the gas under measurement flowing within the gas flow pipe, the introduced gas is discharged from the internal space through the discharge port, the gas under measurement is introduced into the internal space through the introduction port, and the introduced gas is mixed with the ions produced by the ion source, the space forming portion forms the capturing electrode, the space forming portion is configured such that the discharge port has an opening at a distal end of the space forming portion and the introduction port has an opening on an outer circumferential surface thereof at a position located on a proximal end side in relation to the discharge port, and the ion source has a needlelike electrode member having a needlelike distal end portion, and the distal end portion of the needlelike electrode member is located between the introduction port and the discharge port of the space forming portion.

* * * * *